United States Patent [19]
Cyprien et al.

[11] Patent Number: 5,238,679
[45] Date of Patent: Aug. 24, 1993

[54] DIORGANOPOLYSILOXANE DOSAGE FORMS FOR THE CONTROLLED RELEASE OF IODINE VALUES

[75] Inventors: Guy Cyprien, L'Hay les Roses; Alain Fisch, Paris; Johnny Haggiage, Lyons; Hugues Porte, Caluire; Thierry Prazuck, Paris; Ghislaine Torres, Lyons, all of France

[73] Assignee: Rhone-Poulenc Chimie, Courbevoie, France

[21] Appl. No.: 797,158

[22] Filed: Nov. 26, 1991

Related U.S. Application Data

[63] Continuation of Ser. No. 499,551, Mar. 26, 1990, abandoned, which is a continuation of Ser. No. 161,133, Feb. 26, 1988, abandoned.

[30] Foreign Application Priority Data

Feb. 26, 1987 [FR] France ............................ 87 02882

[51] Int. Cl.$^5$ .................. A61K 31/74; A61K 47/30; A61K 33/36
[52] U.S. Cl. .............................. 424/78.25; 424/667; 424/668; 424/669; 424/670; 424/671; 424/672; 424/486; 514/770; 514/772.1
[58] Field of Search ............... 424/78, 80, 486, 78.25, 424/667, 668, 669, 670, 671, 672; 525/474, 387; 514/772.1, 770

[56] References Cited

U.S. PATENT DOCUMENTS

| | | | |
|---|---|---|---|
| 4,012,497 | 3/1977 | Schopflin | 424/432 |
| 4,155,991 | 5/1979 | Schopflin et al. | 424/432 |
| 4,282,207 | 8/1981 | Young et al. | 518/772.1 |
| 4,500,337 | 2/1985 | Young et al. | 424/78 |
| 4,871,547 | 10/1989 | Cyprien et al. | 428/667 |
| 4,888,074 | 12/1989 | Pocknell | 428/432 |
| 5,010,137 | 4/1991 | Umeda et al. | 525/474 |

FOREIGN PATENT DOCUMENTS 1226509 3/1971 United Kingdom ............... 525/174

*Primary Examiner*—Peter F. Kulkosky
*Attorney, Agent, or Firm*—Burns, Doane, Swecker & Mathis

[57] ABSTRACT

Silicone dosage forms adapted for the continuous and controlled release of iodine values, notably to domestic water supplies for the treatment of the various disease states attributed to iodine deficiency, are shaped from (A) a diorganopolysiloxane matrix resin; (B) a reinforcing amount of a filler material ($B_1$) therefor and/or an organic peroxide ($B_2$); and (C) a therapeutically effective amount of at least one water soluble, nontoxic, organic and/or inorganic iodine compound which is in solid or liquid state at ambient temperature.

20 Claims, No Drawings

DIORGANOPOLYSILOXANE DOSAGE FORMS FOR THE CONTROLLED RELEASE OF IODINE VALUES

This application is a continuation of application Ser. No. 07/499,551, filed Mar. 26, 1990, now abandoned, which is a continuation of application Ser. No. 161,133, filed Feb. 26, 1988, now abandoned.

CROSS-REFERENCE TO COMPANION APPLICATIONS

Our copending applications, Ser. No. 4,871,547, Ser. No. 4,886,661, and Ser. No. 5,114,707, all filed concurrently herewith and all assigned of the assignee hereof.

BACKGROUND OF THE INVENTION

1. Field of the Invention

The present invention relates to compositions based on diorganopolysiloxane resins and containing iodine, to dosage forms shaped therefrom and adapted for the controlled release of iodine values, and to a process for treating domestic water supplies and beverages utilizing such compositions/dosage forms.

2. Description of the Prior Art

The number of subjects exhibiting a deficiency or an inadequacy of iodine is currently estimated at several hundred million worldwide. The geographical regions affected to the greatest degree are Latin America, particularly along the Andean Cordillera, and virtually all the non-coastal regions of Africa and of Asia (Pakistan, India, Nepal, China, Laos, etc.).

The principal pathological consequences of iodine deficiency are well known. These are essentially, on the one hand, goiter and its complications, among which may be included swallowing disorders, respiratory disorders, cancer, peripheral circulation and, on the other hand, hypothyroidism and its complications, among which may be mentioned: cretinism, cerebral disorders, premature births, miscarriages and congenital abnormalities.

While iodine deficiency has disappeared from industrialized countries because, for example, the salts used for cooking are iodized, this is not the case in the developing countries, where the two main campaigns undertaken to date have proven ineffective.

These campaigns have for their focus, on the one hand:

(i) the iodination of cooking salt: this is not effective in the majority of the developing countries because very frequently the consumption of salt is minimal, the systems for the distribution of salt via the economic and commercial networks are virtually nonexistent and, finally, in a tropical region, iodine which is added to salt escapes rapidly if it is not perfectly packaged;

and, one the other hand:

(ii) the intramuscular injection of iodinated oil: this injection has the advantage of exhibiting a delayed action, but it is not devoid of disadvantages, particularly the risks of infection, the risks of iodine allergy, and the risks of hyperthyropidism or of hypothyroidism, which are caused by the injection of a necessarily supraphysiological dosage.

Furthermore, Belgian Patent BE-A-889,680 describes the introduction of oligoelements, including iodine, into the drinking water of ruminants, in the form of a dispersion in a binder such as, for example, plaster of Paris. A diorganopolysiloxane may be added with a view to slowing the diffusion of the oligoelement. In addition, the use of iodine and of iodine compounds for disinfecting or for purifying water is well known. Compare, for example, U.S. Pat. Nos. 2,347,567, 2,743,208 and 3,408,295.

There also exist very many patents describing the use of polymeric systems, especially silicone, for the controlled release of an active ingredient, for example by means of a transdermal system (U.S. Pat. No. 4,053,580), or by oral ingestion, especially for ruminants (French Patent FR-A-2,560,768).

Lastly, U.S. Pat. No. 4,384,960 describes placing iodine $I_2$ tablets in a plastic bottle, into which water enters through a porous polymer membrane. The water dissolves the iodine. The purpose of the membrane is merely to prevent the iodine tablets from leaving the bottle.

It is simply suggested, furthermore, that it is possible to introduce iodine $I_2$ into the bottle in a liquid dispersion of silicone or of a dimethylsiloxane elastomer, and then to cur them. This suggested solution is not technically feasible because, firstly, $I_2$ is a well-known inhibitor of the catalysts for curing silicone elastomers capable of being vulcanized at ambient temperature (see, in particular, the publication by W. D. Morain et al., *Plastic and Reconstructive Surgery*, 59, 2, 215-222 (1977)) and, secondly, because of its high volatility, $I_2$ sublimes during the crosslinking of silicone elastomers when heated.

However, in this system, not only is there no control over the release of iodine, but also the iodination of water takes place by noncontinuous or continuous addition of a few drops of highly iodized (to saturation) water contained in the bottle, to any receptacle containing untreated water. It is clear that the solution proposed by U.S. Pat. No. 4,384,960 is imperfect, especially because of the fact that it involves an individual method which, like the intramuscular injection of iodine, requires mass education and mobilization of entire populations.

SUMMARY OF THE INVENTION

Accordingly, a major object of the present invention is the provision of a silicone composition containing iodine and suitable for use for the continuous treatment of water for domestic purposes, particularly in water supply and treatment systems in wells and boreholes. The subject composition makes it possible to distribute (release) a controlled and measured amount of iodine with a view to ensuring the collective treatment of the various manifestations due to an iodine deficiency, as well as a prophylaxis of these various manifestations.

Another object of the invention is to provide a silicone composition containing iodine which, when suitably immersed in water sources to be treated, especially wells and boreholes, continually distributes (releases), preferably for at least one year, an appropriate amount of iodine in a therapeutically active and effective form and dosage in order to treat the various diseases caused by iodine deficiency.

Yet another object of the invention is to provide a silicone composition containing iodine which, when suitably immersed in water sources to be treated, has no undesirable secondary or side effects which are detrimental to the water to be treated from a chemical and biological standpoint.

Still another object is to provide a silicon composition containing iodine, in a form which is adapted to the environment in which the water to be treated is found, this form being particularly adapted to wells and/or boreholes and offering a system for introduction into the wells and/or boreholes permitting it to be easily replaced.

Briefly, the present invention features a silicone composition comprising:

(A) a diorganopolysiloxane resin;
(B) a reinforcing filler ($B_1$) and/or an organic peroxide ($B_2$); and
(C) at least one organic and/or inorganic iodine compound in solid or liquid form at ambient temperature, soluble in water and nontoxic.

DETAILED DESCRIPTION OF THE PREFERRED EMBODIMENTS OF THE INVENTION

More particularly according to the present invention, exemplary of the inorganic iodine compounds, representative are, whether singly or in admixture:

iodides or iodates of the general formulae:

$$(M^{1+})(I^-)_a$$

and $$(M^{1+})(IO_3^-)_a$$

in which a is an integer greater than or equal to 1 and M is a cation selected from among an alkali metal such as sodium and potassium, an alkaline earth metal such as magnesium and calcium, a transition metal such as iron and manganese, a quaternary ammonium $(NY_4)^+$, in which the radicals Y, which may be identical or different, are each a linear or branched chain $C_1$-$C_{20}$ alkyl radical or a hydrogen atom, such as the ammonium ion $NH_4^+$.

The cations $M^{1+}$ and $NY_4^+$ are selected such that the corresponding iodide or iodate is a solid or a liquid at ambient temperature, is soluble in water and is nontoxic.

The iodides and iodates which may be employed are particularly those of the formulae:
NaI, $NaIO_3$,
KI, $KIO_3$,
$MgI_2$, $MgI_2.8H_2O$,
$Mg(IO_3)_2.4H_2O$,
$NH_4I$,
$FeI_2.4H_2O$
$MnI_2$.

These salts may contain water of hydration or water of formation.

As a compound of iodine which is both organic and inorganic, representative is, for example, calcium iodobehenate of the formula:

$$(C_{21}H_{42}ICO_2)Ca$$

Iodinated polyvinylpyrrolidone is exemplary of an organic iodine compound.

For reasons of ease of use, solid iodine compounds are preferred, and NaI and $KIO_3$ are the most preferred among these.

All the iodine compounds such as defined above release iodine in a nontoxic and therapeutically effective form when they are dissolved in the water to be treated.

By "nontoxic iodine compound" according to the invention is intended a compound which, in solution, is not toxic in the dosages contemplated hereby.

By "water-soluble iodine compound" is intended a compound having a solubility of at least 100 µg/l at ambient temperature.

From 5 to 150 parts and preferably from 10 to 100 parts of iodine compound (C) are generally employed per 100 parts of the resin (A).

In the developing countries in particular, water for domestic use (drinking, washing, irrigation, and the like) is essentially provided by structures of two types, wells and boreholes.

For obvious reasons of cost, efficiency and salubriousness, the creation of a new water source is frequently produced by drilling.

A borehole is a column of air drilled through compact rock formations having a depth which is generally between 20 and 100 meters and a diameter of at least approximately 10 cm. Water filters into this column through cracks or various interstices. The water reserve which is immediately available thus consists of a column of 10 to 70 meters, generally from 30 to 50 meters, in height, which is withdrawn with the aid of an immersed-body pump.

This water is renewed chiefly as a function of the use of the borehole, which depends on the season. In fact, in the rainy season the borehole is traditionally used less. On the other hand, in the dry season the borehole is used for approximately 10-12 hours daily, which is a quantity of between 5 and 10 m³ per day for approximately six months.

As a general rule, a well may be run dry twice daily in the dry season, which corresponds to a maximum usage of 5 to 10 m³, based on these average statistical data.

Numerous studies show that in the regions of the world which are highly endemic in goiter, the preexisting proportion of iodine equivalent in the water in boreholes or in wells is less than 2 micrograms per liter (2 µg/l). It is currently estimated that a daily input of approximately 100 µg of iodine equivalent per day per person would be sufficient to prevent the development of endemic goiter and doubtless approximately 150 µg in the presence of regular consumption of goiterogenic substances. Conversely, acute iodine intoxication may be responsible for neurological irritation, for hyperthyroidism or for hypothyroidism.

It is assumed in the medical arts that the ingestion of a dose of 3 grams of iodine equivalent by an adult subject, as a single dose, does not produce any secondary effect.

Consequently, the objective is to make it possible to provide an individual with 20 to 200 µg, preferably approximately 100 µg, of iodine equivalent daily.

Thus, with the knowledge that, on average, an adult individual ingests 2 liters of water daily and on the basis of the above data (a borehole with an output of 600 l/hr), it appears desirable that one liter of treated water should contain approximately 50 µg/l of iodine, which corresponds to 50 µg of iodine equivalent per liter per person, which requires the silicone composition to release 720 mg/d of iodine equivalent, i.e., 270 g of iodine equivalent to be released over one year.

Unless indicated otherwise, the parts and percentages given herein are by weight.

Surprisingly and unexpectedly, it has now in fact been found, according to the present invention, that it is possible to incorporate into a silicone resin large quantities of iodine compound in a solid or liquid form such as defined above, namely from 5 to 150 parts, preferably from 20 to 100 parts per 100 parts of a diorganopolysiloxane resin filled with a reinforcing filler, and thus to obtain a product which, even in the absence of a crosslinking and/or antistructuring agent has sufficient mechanical characteristics for the intended application and which makes it possible to ensure a continuous and controlled release of iodine, preferably for at least one year, when immersed in water.

The controlled iodine release system forms part of the matrix systems in which the diffusion of the active ingredient is normally determined by Fick's Law, that is to say, by diffusion kinetics on the order of ½ for only 60% by weight of the active principal. Beyond 60% the matrix is exhausted and the diffusion fluxes ar greatly reduced. Surprisingly and unexpectedly, it has been found that the silicone matrix system according to the invention continuously releases iodine according to zero-order kinetics and does so until 80% by weight and more of the iodine compound has been released.

The considerable advantage contributed by the silicone matrix is, therefore, that it is very easy to extrapolate the continuous diffusion of the active ingredient after a measurement of the quantity released after at least one month, because it is known that the diffusion kinetics are of zero order and that at least 80% of the iodine compound will be released according to these kinetics.

In order to gain complete control of the release of the active ingredient, it is advantageous to shape the silicone matrix in the form of elementary modules (elements) of various shapes such as cubes, right parallelepipeds, cylinders and spheres, whose fundamental parameters are the following:

(a) the nature of the iodine compound;
(b) the mean diameter (particle size) g of the particles of the iodine compound in the preferred case where the latter is a solid;
(c) the concentration of the iodine compound within the matrix;
(d) the surface/volume ratio R of the module.

The nature of the iodine compound and its particle size define the rate of diffusion of the active ingredient through the matrix.

The lower the value of g, the slower v is and vice versa.

The higher the value of t, the greater the flux of active ingredient and vice versa.

The higher the value of R, the greater the high flux of active ingredient and vice versa.

One skilled in this art, using routine experiments, is capable of rapidly and without difficulty obtaining the required result by extrapolating the theoretical elution time which will correspond to the actual time of diffusion of the active ingredient.

In the case of NaI and KIO$_3$, which are the preferred iodine compounds, g, t and R may advantageously be within the following ranges:

(i) g of from 1 to 300 μm;
(ii) t of from 10 to 100 parts by weight of iodine compound per 100 parts of (A); and
(iii) R of from 0.5 to 50 in the case of a cylindrical shape.

It is desirable, furthermore, that the iodine compound should be dispersed homogeneously throughout the matrix.

More preferably, the present invention relates to a silicone composition comprising:

(A): 100 parts of a diorganopolysiloxane resin having a viscosity greater than 1 million mPa.s at 25° C.;
(B): 5 to 130 parts of a reinforcing, preferably siliceous, filler (B$_1$), selected from among pyrogenic silicas and precipitated silicas, and/or from 0.1 to 6 parts of an organic peroxide (B$_2$); and
(C) 5 to 150 parts of an organic and/or inorganic iodine compound, solid at ambient temperature, soluble in water and nontoxic.

More particularly, the diorganopolysiloxane resin (A) has the general formula $R_{3-a}(R'O)_a SiO(R_2SiO)_n Si(OR')_a R_{3-a}$, in which the symbols R, which may be identical or different, denote C$_1$–C$_8$ hydrocarbon radicals, substituted or otherwise by halogen atoms or cyano radicals, the symbol R' denotes a hydrogen atom or a C$_1$–C$_4$ alkyl radical, the symbol a denotes zero or one, and the symbol n denotes a number having a sufficient value to provide a viscosity of at least 1 million mPa.s at 25° C., and at least 50% of the number of radicals denoted by R are methyl radicals.

0.005 to 0.5 mole % of the units constituting the resin (A) are preferably selected from those of the formulae $(CH_2=CH)(R)SiO$ and/or $(CH_2=CH)R_{2-a}(R'O)_a SiO_{0.5}$.

The resin (A) having a viscosity of 1 million mPa.s at 25° C., preferably of at least 2 million mPa.s at 25° C., comprises, along its chain, R$_2$SiO units and it is blocked by an $R_{3-a}R(O)_a SiO_{0.5}$ unit at each end of its polymer chain. However, the presence of units of different structure, mixed with these units, for example of formula RSiO$_{1.5}$ and SiO$_2$, is also within the scope of the invention, in the proportion of not more than 2% based on the total number of the R$_2$SiO and $R_{3-a}(RO')_a SiO_{0.5}$ units.

The symbol R denotes a C$_1$–C$_8$ hydrocarbon radical substituted or otherwise by halogen atoms or cyano radicals. More specifically, it includes:

(1) C$_1$–C$_5$ alkyl radicals, substituted or otherwise by halogen atoms or cyano radicals, such as methyl, ethyl, propyl, isopropyl, butyl, isobutyl, pentyl, 3,3,3-trifluoropropyl, β-cyanoethyl and τ-cyanopropyl radicals,;
(2) C$_2$–C$_4$ alkenyl radicals such as vinyl, allyl and 2-butenyl radicals; and
(3) C$_6$–C$_8$ monocyclic aryl radicals, substituted or otherwise by halogen atoms, such as phenyl, chlorophenyl, The C$_1$–C$_4$ alkyl radicals denoted by the symbol R, are more specifically methyl, ethyl, propyl, isopropyl, butyl and secondary butyl radicals.

At least 50% on a numerical basis, preferably at least 70%, of the radicals denoted by R are methyl radicals.

Furthermore, vinyl radicals are also preferably present in a suitable quantity in the resin (A). They constitute units of the formula $CH_2=CH(R)SiO$ and $CH_2=CH(R_{2-a})(R'O)_a SiO_{0.5}$, whose number represents 0.005 to 0.5 mole %, preferably 0.01 to 0.45 mole %, of the total of the units of general formulae R$_2$SiO and $R_{3-a}(R'O)_a SiO_{0.5}$ which constitute the resin (A).

By way of specific examples of units constituting the resins (A), representative are those of the formulae:
$(CH_3)_2SiO$,
$CH_3(CH_2=CH)SiO$,
$CH_3(C_6H_5)SiO$,
$(C_6H_5)_2SiO$,
$CH_3(C_2H_5)SiO$,
$CH_3CH_2-CH_2(CH_3)SiO$, $CH_3(n-C_3H_7)SiO$,
$(CH_3)_3SiO_{0.5}$,
$(CH_3)_2(CH_2=CH)SiO_{0.5}$,
$CH_3(C_6H_5)_2SiO_{0.5}$,
$CH_3(C_6H_5)(CH_2=CH)SiO_{0.5}$,
$HO(CH_3)_2SiO_{0.5}$,
$CH_3O(CH_3)_2SiO_{0.5}$,
$C_2H_5O(CH_3)_2SiO_{0.5}$,
$n-C_3H_7O(CH_3)_2SiO_{0.5}$,
$HO(CH_2=CH)(CH_3)SiO_{0.5}$.

The resins (A) are commercially available from the various manufacturers of silicones; furthermore, they may be readily prepared using methods which are abundantly well described in the chemical literature.

In the majority of cases, methylvinyldimethylpolysiloxane resins are used containing $(CH_3)_2SiO$ and $CH_2=CH(CH_3)SiO$ recurring units along their polymer chain and, at the ends of the polymer chain, units selected from among those of the formulae: $(CH_3)_2(CH_2=CH)SiO_{0.5}$, $HO(CH_3)(CH_2=CH)SiO_{0.5}$, $(CH_3)_3SiO_{0.5}$, $C_6H_5(CH_3)(CH_2=CH)SiO_{0.5}$, $HO(CH_3)_2SiO_{0.5}$, or dimethylpolysiloxane resins blocked at each end of their polymer chain by one of the above units containing a vinyl radical.

They generally have a viscosity of at least 2 million mPa.s at 25° C.

The fillers $(B_1)$ which are preferably reinforcing silicas are employed in a proportion of 5 to 130 parts pe 100 parts of diorganopolysiloxane resins (A). They are selected from among pyrogenic silicas and precipitated silicas. They have a specific surface area, measured according to the BET method, of at least 50 $m^2/g$, preferably greater than 70 $m^2/g$, a mean dimension of the primary particles of less than 0.1 $\mu m$ (micrometer) and an apparent density of less than 200 g/liter.

These silicas may be incorporated as such or after they have been treated with the organosilicon compounds usually employed for this purpose. These compounds include methylpolysiloxanes such as hexamethyldisiloxane and octamethylcyclotetrasiloxane, methylpolysilazanes such as hexamethyldisilazane and hexamethylcyclotrisilazane, chlorosilanes such as dimethyldichlorosilane, trimethylchlorosilane, methylvinyldichlorosilane and dimethylvinylchlorosilane, and alkoxysilanes such as dimethyldimethoxysilane, dimethylvinylethoxysilane and trimethylmethoxysilane. In the course of this treatment, the silicas may increase in their initial weight up to a proportion of 20%, preferably approximately 18%.

The compositions according to the invention may be kneaded cold, as such, and may be extruded, for example, in the form of a cylinder with a diameter of from 0.5 to 9 cm. The cylinders of silicone composition which are obtained may be cut to the desired length in the case of their utilization in boreholes, such that the cylinder contains a sufficient quantity of iodine equivalent for release over the course of one year.

It has surprisingly been found that these uncrosslinked silicone compositions have physical characteristics which are sufficient for the intended applications and release iodine in a continuous and controlled manner. An organic peroxide $(B_2)$ may be employed within the scope of the present invention, in addition to $(B_1)$ or instead of $(B_1)$ or at the same time as $(B_1)$. The elastomeric composition must then be cross-linked when hot. [The organic peroxides $(B_2)$ are employed in a proportion from 0.1 to 6 parts, preferably 0.2 to 5 parts, per 100 parts of the resins (A). They are well known to this art and include, more especially, benzoyl peroxide, 2,4-dichlorobenzoyl peroxide, dicumyl peroxide, 2,5-bis(t-butylperoxy isopropyl carbonate, di-t-butyl peroxide and 1,1-bis(t-butylperoxy)-3,3,5-trimethylcyclohexane.

These various peroxides decompose at temperatures and at rates which are sometimes different. They are selected as a function of the required cure conditions.

The silicone compositions according to the invention may additionally contain, per 100 parts of resin (A), from 0.1 to 6 parts of an antistructuring agent (D) which is an organic fluorine polymer in the form of a pulverulent solid.

The fluorine polymers (D) are employed in a proportion of 0.1 to 6 parts, preferably 0.15 to 5 parts, per 100 parts of the diorganopolysiloxane resins (A). These compounds are also well known to this art: they are prepared by polymerization of copolymerization of monomers selected, for example, from among tetrafluoroethylene, chlorotrifluoroethylene, vinylidine fluoride and hexafluoropropene. They are therefore polymers or copolymers of units derived from the above-mentioned monomers; polytetrafluoroethylenes, binary copolymers of the polytetrafluoroethylene/beta-fluoropropene or of the vinylidine fluoride/hexafluoropropene type, and ternary copolymers of the vinylidine fluoride/hexafluoropropene/tetrafluoroethylene type may thus be employed.

These compounds may be introduced into the compositions of the invention in the form of powders having a mean particle diameter of less than 100 micrometers, for example having a diameter ranging from 25 to 65 micrometers.

When the crosslinking agents $(B_2)$ are employed, preferably up to 90% by weight of the reinforcing silicas (C) may be replaced with semireinforcing or extender fillers whose particle diameter is greater than 0.1 $\mu m$, such as ground quartz, calcined clays and diatomaceous earths.

The silicone compositions may additionally comprise from 1 to 10 parts of dimethylpolysiloxane oils (E) with silanol end groups and having a viscosity of from 10 to 5,000 mPa.s, preferably from 30 to 1,000 mPa.s, at 25° C., per 100 parts of resin (A). Their use is especially recommended when the quantities of reinforcing fillers $(B_1)$ are high.

The preparation of the compositions according to the invention is carried out using known mechanical means, for example dough mixers, roll mills and screw mixers.

The various constituents are incorporated in such apparatus in an order which may be immaterial. It is recommended, nevertheless, to charge the resin (A) and then, in order, the siliceous fillers $(B_1)$ and the iodine compound (C), the additive (E) if desired and, lastly, the compound (D) and $(B_2)$.

The compositions obtained are stable in storage; furthermore, they are easily molded and extruded, and this permits very varied shapes to be produced. Those containing peroxide $(B_2)$ are cross linked by heating. The heating time obviously varies with the temperature, the pressure and the nature of the crosslinking agents. It is generally on the order of a few minutes at about 150° to 250° C. and of a few seconds at about 250° to 350° C.

The elastomers formed in this manner may be subsequently post-heated if desired, particularly those obtained by molding for a period of at least one hour at a temperature of between 190° and 270° C. with the objective of completing their cross linking.

Nevertheless, as soon as their first crosslinking stage is finished, namely, prior to any post-heating stage, these elastomers have sufficient physical characteristics for the intended application.

The silicone compositions, optionally crosslinked are advantageously in the form of modules (elements) of various shapes. The quantity of iodine and the release period are determined for a given module.

Thus, an appropriate number of modules may be immersed in the water to be treated, which corresponds to a quantity (a weight of elastomer) such that the elastomer ensures a continuous and controlled release of iodine, preferably for at least one year. At the end of this period, the modules (elements) are replaced.

It has surprisingly been found that these silicone compositions, optionally crosslinked, have sufficient physical characteristics for the intended applications.

In order to further illustrate the present invention and the advantages thereof, the following examples are given, it being understood that same are intended only as illustrative and in nowise limitative.

EXAMPLE 1

Preparation of the Composition

Composition: the following ingredients were intimately mixed using a kneader.

(i) 100 parts of a dimethylmethylvinylpolysiloxane resin (A) blocked by a trimethylsiloxy unit at each of the two polymer ends and containing 99.8 mol % of dimethylsiloxy units and 0.2 mol % of vinylmethylsiloxy units in its chain and having a viscosity of 10 million mPa.s at 25° C.;

(ii) 43.5 parts of filler (B) which was a D4 (octamethylcyclotetrasiloxane)-treated pyrogenic silica having a BET specific surface area of 300 m$^2$/g;

(iii) 1 part of a linear dimethylpolysiloxane blocked with dimethylhydroxysiloxane groups at both of the polymer and having a viscosity of 50 mPa.s;

(iv) 0.2 part of octamethyltetracyclosiloxane;

(v) 37.2 parts of NaI of mean particle size equal to 5 μm (C).

The kneading was stopped 30 minutes upon completion of the addition of silica. The homogeneous composition which had just been prepared was removed from the kneader and is referred to herein as the master mixture (MM).

The MM was transferred to a roll mill in order to incorporate, per 100 parts of MM:

0.5 part of 2,5-dimethyl-2,5-di(tert-butylperoxy)hexane.

The catalyzed composition separated readily from the mill rolls. It was then extruded into a continuous sausage 26 mm in diameter which was then cured by being passed through a 6-m oven heated to 350° C. at a speed of 1 m per minute. A uniform rod was obtained, which was then reheated for 4 hours at 150° C.

Experimental Protocol for Measuring Elution Kinetics

The elastomeric composition containing NaI was cut to the desired length (35.4 mm), in accordance with the surface/volume ratio (2.08 cm$^{-1}$) desired to be obtained and was immersed in a container of 500 ml of distilled water, thermostated at 20° C.

The container was equipped with a magnetic stirring system driven in a slow rotary motion (100 rev/min) ensuring the homogeneity of the solution. It was covered with a lid in order to reduce water evaporation to a minimum.

1-ml samples were taken daily during the initial period of elution, and weekly after two weeks of elution.

The concentration of iodide or iodate, released daily, was determined by measurement using an iodide-specific electrode:

Two milliliters of a solution ($K_2SO_4$ = ascorbic acid) were added to one milliliter of a sample from the container—this solution served as an ion buffer and as a reducing solution in the case where iodates were being measured—together with one milliliter of distilled water. The electrode was immersed in this solution and the electrochemical potential of the solution was measured. A calibration curve established beforehand using iodide solutions containing $5 \times 10^{-5}$ M/l (M: mole) to $5 \times 10^{-2}$ M/l enabled the iodide or iodate concentration (C) to be calculated in mg/L of the solution.

The characteristics of the immersed cylinder were:

| The characteristics of the immersed cylinder were: | |
| --- | --- |
| Diameter | 26.3 mm |
| Height | 35.4 mm |
| Surface area | 40.1 cm$^2$ |
| Volume | 19.23 cm$^3$ |
| S/V | 2.08 cm$^{-1}$ |
| Total Weight | 19.89 g |
| Initial quantity of I(Qo) | 3.36 g |

The results of the solution kinetics are reported in Table I.

Q corresponds to the quantity of I equivalent (designated as "active ion") eluted at time t.

With the knowledge that 80% of the active ion incorporated was eluted in accordance with zero-order kinetics with time, the theoretical elution time (Te) for each example was calculated according to:

$$Te = \frac{0.8 \times Qo}{\text{Daily flow}} \text{ (days)}$$

In the case of this Example, Te was 640 days.

TABLE I

| TIME (DAY) | Cumulative Q (gram) active ion | 100*Q/QO % |
| --- | --- | --- |
| 0.19 | 0.189 | 5.60 |
| 0.98 | 0.297 | 8.81 |
| 2.01 | 0.341 | 10.13 |
| 6.92 | 0.355 | 10.53 |
| 11.02 | 0.358 | 10.62 |
| 15.92 | 0.428 | 12.70 |
| 17.92 | 0.440 | 13.08 |
| 24.97 | 0.431 | 12.79 |
| 35.20 | 0.432 | 12.83 |
| 45.91 | 0.535 | 15.89 |
| 52.23 | 0.468 | 13.89 |
| 60.19 | 0.522 | 15.50 |
| 73.21 | 0.622 | 18.45 |
| 77.12 | 0.622 | 18.47 |
| 91.12 | 0.602 | 17.86 |
| 115.92 | 0.712 | 21.13 |
| 150.18 | 0.726 | 21.56 |

EXAMPLE 2

The composition employed was the same as in Example 1, except that 37.2 parts of $KIO_3$ were incorporated, having a particle size of from 100 to 200 μm.

The kneading was stopped 30 minutes upon completion of the addition of silica. The homogeneous composition which had just been prepared was removed from the kneader and is referred to herein as the master mixture (MM).

The MM was transferred to a roll mill in order to incorporate, per 100 parts of (MM):

0.5 part of 2,5-dimethyl-2,5-di(tert-butylperoxy)-hexane.

The catalyzed composition separated readily from the mill rolls. It was then extruded into a continuous sausage 23 mm in diameter which was then cured by being passed through a 6-m oven heated to 350° C. at a speed of 1 m per minute. A uniform rod was obtained, which was then reheated for 4 hours at 150° C.

A cylinder was then cut therefrom, the characteristics of which were as follows:

| A cylinder was then cut therefrom, the characteristics of which were as follows: | |
|---|---|
| Diameter | 23.0 mm |
| Height | 50.0 mm |
| Surface area | 44.4 cm² |
| Volume | 20.76 cm³ |
| S/V | 2.14 cm⁻¹ |
| Total Weight | 25.37 g |
| Initial quantity of I(Qo) | 3.01 g |

The results of the elution kinetics are reported in Table II.

The theoretical elution time of this Example was 1170 days.

TABLE II

| TIME (DAY) | Cumulative Q (gram) active ion | 100*Q/QO % |
|---|---|---|
| 0.12 | 0.009 | 0.31 |
| 0.29 | 0.010 | 0.34 |
| 1.00 | 0.018 | 0.58 |
| 2.00 | 0.022 | 0.71 |
| 6.00 | 0.035 | 1.15 |
| 8.00 | 0.045 | 1.45 |
| 12.00 | 0.051 | 1.66 |
| 15.00 | 0.053 | 1.74 |
| 21.00 | 0.065 | 2.12 |
| 26.00 | 0.071 | 2.32 |
| 33.00 | 0.0S2 | 2.67 |
| 40.00 | 0.091 | 2.98 |
| 49.00 | 0.104 | 3.41 |
| 61.00 | 0.116 | 3.7S |
| 79.00 | 0.141 | 4.60 |
| 96.00 | 0.161 | 5.24 |
| 117.00 | 0.182 | 5.92 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A cured silicone composition adapted for the controlled release of iodine values, comprising (A) a diorganopolysiloxane matrix having a viscosity of at least 1,000,000 mPa.s at 25° C. (B) an organic peroxide; and (C) a therapeutically effective amount of at least one water soluble, nontoxic organic and/or inorganic iodine compound which is in solid or liquid state at ambient temperature, said iodine compound being dispersed homogeneously throughout the composition and said diorganopolysiloxane being cross-linked by said organic peroxide.

2. The silicone composition as defined by claim 1, comprising from 5 to 150 parts of the iodine compound (C) per 100 parts of the resin (A).

3. The silicone composition as defined by claim 1, wherein the iodine compound (C) comprises an iodide or iodate of the general formulae:

$$(M^{a+})(I^-)_a$$

and $$(M^{a+})(IO_3^-)_a$$

in which a is an integer greater than or equal to 1 and M is an alkali or alkaline earth metal, a transition metal, or a quaternary ammonium $(NY_4)^+$ cation, in which the latter radicals Y, which may be identical or different, are each a linear or branched chain $C_1$–$C_{20}$ alkyl radical or a hydrogen atom.

4. The silicone composition as defined by claim 1, wherein the iodine compound (C) comprises NaI, NaIO$_3$, KI, KIO$_3$, MgI$_2$, M$_g$I$_2$.8H$_2$O, Mg(IO$_3$)$_2$.4H$_2$O, NH$_4$I, FeI$_2$.4H$_2$O or MnI$_2$.

5. The silicone composition as defined by claim 1, wherein the iodine compound (C) comprises calcium iodobehenate.

6. The silicone composition as defined by claim 1, wherein the iodine compound (C) comprises iodinated polyvinylpyrrolidone.

7. The silicone composition as defined by claim 1, where the resin (A) has the general formula $R_{3-a}(R'O)_a SiO(R_2SiO)_n Si(OR')_a R_{3-a}$, in which the symbols R, which may be identical or different, are each a $C_1$–$C_8$ hydrocarbon radical or a substituted such radical bearing at least one halogen atom or cyano radical substituent, the symbol R' is a hydrogen atom or a $C_1$–$C_4$ alkyl radical, the symbol a is zero or one, and the symbol n is a number such as to provide a viscosity of at least 1 million mPa.s at 25° C., and at least 50% of the number of radicals R being methyl radicals.

8. The silicone composition as defined by claim 7, wherein from 0.005 to 0.5 mol % of the recurring units constituting the resin (A) comprise those of the formulae $(CH_2=CH)(R)SiO$ and $(CH_2=CH)R_{2-a}(RO')_a SiO_{0.5}$.

9. The silicone composition as defined by claim 1, further comprising from 0.1 to 6 parts of an antistructuring agent (D) which comprises an organic fluorine polymer in the form of a pulverulent solid.

10. A shaped article comprising the silicone composition as defined by claim 1.

11. The shaped article as defined by claim 10, adapted to controlledly and continuously release about 50 μg of iodine equivalent per liter, to an external aqueous environment.

12. A method for the treatment, in mammalian organisms in need of such treatment, of disease states attributed to iodine deficiency, comprising adding to the water or beverage supply thereof, at least one shaped article as defined by claim 10, such as to controlledly and continuously release therapeutically effective amounts of iodine equivalent thereto.

13. A cured silicone composition adapted for the controlled release of iodine values, comprising (A) a diorganopolysiloxane gum having a viscosity of at least 1,000,000 mPa.s at 25° C., (B) an organic peroxide; and (C) a therapeutically effective amount of at least one water soluble, nontoxic, organic and/or inorganic iodine compound which is in solid or liquid state at ambient temperature, said iodine compound being dispersed homogeneously throughout the composition and said diorganopolysiloxane being cross-linked by said organic peroxide, said composition making it possible to ensure a continuous and controlled release of iodine according to zero-order kinetics when immersed in water.

14. The silicone composition as defined in claim 1, further comprising (B) a reinforcing amount of a filler material.

15. The silicone composition as defined in claim 13, further comprising (B) a reinforcing amount of a filler material.

16. The silicone composition as defined in claim 1, wherein component (B) comprises a siliceous reinforcing filler material.

17. The silicone composition as defined by claim 14, comprising:

(A) 100 parts by weight of a diorganopolysiloxane resin having a viscosity of at least 1 million mPa.s at 25° C.;
(B) 0.1 to 6 parts of an organic peroxide and 5 to 130 parts by weight of a pyrogenic or precipitated silica reinforcing siliceous filler material;
(C) 5 to 150 parts by weight of a water soluble, nontoxic, organic and/or inorganic iodine compound which is in solid state at ambient temperature.

18. The silicone composition as defined by claim 14, comprising from 0.1 to 6 parts (B) of an organic peroxide.

19. The silicone composition as defined by claim 14, up to 90% by weight of the reinforcing silicone filler material comprising a semireinforcing or extending filler.

20. The silicone composition as defined by claim 1 wherein said gum continuously releases iodine according to zero-order kinetics until at least 80% by weight of the iodine compound has been released.

* * * * *